(12) United States Patent
Niazi

(10) Patent No.: US 9,101,857 B2
(45) Date of Patent: Aug. 11, 2015

(54) GAS SCRUBBED PERFUSION FILTER

(75) Inventor: Sarfaraz Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 161 days.

(21) Appl. No.: 13/093,859

(22) Filed: Apr. 26, 2011

(65) Prior Publication Data

US 2011/0201050 A1 Aug. 18, 2011

(51) Int. Cl.
| | |
|---|---|
| *B01D 29/64* | (2006.01) |
| *C12M 1/12* | (2006.01) |
| *C12M 1/04* | (2006.01) |
| *B01D 29/11* | (2006.01) |
| *A01N 1/02* | (2006.01) |
| *C12M 1/00* | (2006.01) |

(52) U.S. Cl.
CPC .............. *B01D 29/64* (2013.01); *A01N 1/0247* (2013.01); *B01D 29/114* (2013.01); *C12M 23/26* (2013.01); *C12M 29/04* (2013.01); *C12M 29/10* (2013.01)

(58) Field of Classification Search
CPC .. B01D 65/02; B01D 2321/185; B01D 29/64; B01D 29/114; C02F 2303/20; C12M 29/04; C12M 29/10; C12M 23/26; A01N 1/0247
USPC ........... 210/200–203, 209, 220, 221.1–221.2, 210/252–257.2, 258, 275, 314, 319, 321.6, 210/321.79, 321.8, 321.88, 321.89, 500.23, 210/323.1, 323.2, 333.01, 340, 344, 391, 210/393, 407, 408, 411, 416.1, 486, 488, 210/496, 500.1, 500.27, 503, 504, 506; 435/382, 383, 393, 395, 401
See application file for complete search history.

(56) References Cited

U.S. PATENT DOCUMENTS

| | | | | |
|---|---|---|---|---|
| 3,968,034 | A * | 7/1976 | Tymoszczuk | 210/618 |
| 5,236,595 | A * | 8/1993 | Wang et al. | 210/669 |
| 5,443,985 | A | 8/1995 | Lu et al. | |
| 6,193,890 | B1 * | 2/2001 | Pedersen et al. | 210/636 |
| 6,245,239 | B1 * | 6/2001 | Cote et al. | 210/636 |
| 6,303,035 | B1 * | 10/2001 | Cote et al. | 210/636 |
| 6,375,848 | B1 * | 4/2002 | Cote et al. | 210/650 |
| 6,544,788 | B2 | 4/2003 | Singh | |
| 6,613,222 | B2 * | 9/2003 | Mikkelson et al. | 210/138 |
| 7,179,370 | B2 * | 2/2007 | Dimitriou et al. | 210/151 |
| 7,241,382 | B2 * | 7/2007 | Gordon | 210/209 |
| 7,468,082 | B2 * | 12/2008 | Gordon | 55/302 |
| 7,981,301 | B2 * | 7/2011 | Powell | 210/748.01 |

\* cited by examiner

*Primary Examiner* — John Kim
(74) *Attorney, Agent, or Firm* — Sarfaraz K. Niazi; Cheryl Liljestrand

(57) ABSTRACT

Fine gas bubbles traveling at fast speed are employed to scrub a hard-surface filter for harvesting liquids from suspensions including those consisting of nutrient media and cell culture, on a continuous basis without clogging the filters.

16 Claims, 2 Drawing Sheets

GAS SCRUBBED PERFUSION FILTER

FIELD OF THE INVENTION

The present invention generally relates to systems and methods for perfusion operations in a bioreactor. The invention has applications in the culture of animal, insect, and plant cells, for the production of secreted substances such as proteins, antibodies, polypeptides, and viruses. Applications include medical areas such as artificial organs and cell therapy.

BACKGROUND OF THE INVENTION

Cell culture has generated considerable interest in recent years due to the revolution in genetic engineering and biotechnology. Cells are cultured to make proteins, receptors, vaccines, and antibodies for therapy, research, and for diagnostics.

One limitation to the use of this technology is the high cost of operation. Traditionally, cell culture has been operated in a batch mode. In batch operation, the bioreactor is seeded with a small amount of cells and the cells are grown to high density. The cells secrete the product of interest and eventually die due to lack of nutrients at which point the culture is harvested. This method has several drawbacks: firstly, a large fraction of nutrients are wasted in simply growing up cells and are not used directly for making the product; secondly, product formation is often inhibited due to the buildup of toxic metabolic byproducts; and lastly critical nutrients are often depleted leading to low cell densities and consequently lower product yields.

It has long been recognized that perfusion culture offers better economics. In this operation, cells are retained in the bioreactor, and the product is continuously removed along with toxic metabolic byproducts. Feed, containing nutrients is continually added. This operation is capable of achieving high cell densities and more importantly, the cells can be maintained in a highly productive state for weeks and even months. This achieves much higher yields and reduces the size of the bioreactor necessary. It is also a useful technique for cultivating primary or other slow growing cells.

The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential.

The current use of perfused culture is in response to the challenge of growing cells at high densities (i.e., $0.1\text{-}5 \times 10^8$ cells/ml). In order to increase densities beyond $2\text{-}4 \times 10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

Perfusion cell culture has long been used as a method of achieving higher cell densities and increased culture length when compared to batch culture methods. The greater cell density and longer culture life can result in better yields of secreted products, more efficient use of media and the ability to generate large numbers of cells in small volumes. The greatest challenge of perfusion cell culture has always been the need to contain the cells within the culture without reducing cell viability. Filters have traditionally been used to contain the cells, and elaborate methods have been devised to prevent the filters from fouling and shortening the length of the perfusion culture. All of these steps add substantial cost to the manufacturing process.

The U.S. Pat. No. 5,443,985 suggests that to prevent the clogging of the perfusion filter, it should be placed in the upper part of an inclined bioreactor where it is less likely to encounter the cells that might block the filter.

The U.S. Pat. No. 6,544,788 to Singh discloses a perfusion filter with neutral buoyancy that allows this 'lily pad' filter to float just under the surface of the media where the wave action that mixes and oxygenates the culture helps wash the filter. The gentle washing prevents the filter from clogging and extends the length of the perfusion culture while maintaining a low shear environment for the cells. This invention is of little use in bioreactors where the suspension culture is maintained rather homogenous throughout the bioreactor obviating any advantage of keep the filter floating at the surface where the cell count is expected to be the lowest; this may be of some value in rocking platform bioreactors like the GE Wave Bioreactor but for large scale suspension culture where the cells are kept in uniform suspension, both of the above prior art disclosures are of little practical value.

The development of a perfused packed-bed reactor using a bed matrix of a non-woven fabric has provided a means for maintaining a perfusion culture at densities exceeding $10 \times 10^8$ cells/ml of the bed volume (CelliGen, New Brunswick Scientific, Edison, N.J.). However, like other such methods, these devices have high cost and limited applications.

Perfusion operations have tremendous potential for growing the large number of cells needed for human cell and genetic therapy applications.

The central problem in perfusion culture is how to retain the cells in the bioreactor. Prior art can be classified into four basic separation technologies: filtration, gravity sedimentation, centrifugation and continuous perfusion. Filtration methods require some means to keep the filter from clogging over the required weeks of operation. Cross-flow filters are typically used. Here a high tangential liquid velocity is used to keep the surface clean. Spinning filters are another embodiment of this concept. Gravity sedimentation can be used to separate the cells and several types of inclined settlers have been reported. The major problem with settlers is the varying sedimentation characteristics of different cells and the difficulty in scale-up to industrial systems. Centrifugation has found limited application in cell culture due to the difficulty in maintaining sterility.

The first three methods share a common weakness—in that the liquid from the bioreactor must be pumped through the separation device and the cell-enriched material returned to the bioreactor. Keeping this recirculation loop sterile is difficult, and contamination often occurs. To maintain the high cross-flow velocity necessary to prevent clogging, the cells are subjected to high pumping shear in the recirculation loop and are often damaged. Oxygen depletion can also occur if the pumping rate is too slow. These factors often lead to degradation in product quality and quantity. The fourth type of method avoids some of these problems by eliminating the need to use a pump-around loop wherein nutrient media is removed from the bioreactor and replaced with fresh media by filtering the contents of the bioreactor continuously.

However, the method of removing nutrient media from a bioreactor and replacing it with fresh media becomes a difficult process when using thousand of liters of nutrient media and very high density of cell culture, as it is becoming a normal exercise in commercial production. Whether it is placing the filter in a special place in the bioreactor to reduce exposure to high cell titer or gently shaking the filter to keep the filter from getting clogged, these prior art methods are inadequate for large-scale commercial production. Even if the perfusion is performed at a rate of one to two media volume exchanged per day, bioreactors containing thousands of liters with suspension culture at high titer would make it impossible to use any of the current art to accomplish the filtration and harvesting of the nutrient media. Large-scale filtration would require faster passage of media through the filter and that would inevitably bring cell culture in direct contact with filter surface resulting in fouling and blockage of the filters. Unfortunately, the flexible and disposable bioreactors wherein most of the art of perfusion filtration is developed are not suitable for large-scale operations and thus the dearth of technology in the field of cell culture processing was not fully appreciated.

There is therefore a dire need to invent systems useful for any size of operation, ones that could not be blocked regardless of the rate of filtration and ones that could be sterilized and be also affordable. The instant invention resolves all of these problems by utilizing a method scrubbing the filter surface by fine bubbles of, which in itself may help growth of cell culture.

SUMMARY OF THE INVENTION

The present invention solves the problem of filter clogging in perfusion bioreactors by a novel filter assembly design. The filter assembly of the instant invention comprises two parts: a perfusion filter and a sparging filter. The perfusion filter of the instant invention is placed in such proximity to the sparging filter that the fine bubbles produced by the sparging filter continuously scrub it. To make the perfusion faster, the entire surface of the perfusion filter consists of a liquid permeable, but cell-retentive surface or an installed membrane. This is in clear contrast to the invention disclosed in U.S. Pat. No. 6,544,788 where only a limited bottom area of the filter has the permeability, severely restricting its application.

A flexible tube (harvesting tube) allows the essentially cell-free filtrate to be drawn out from inside the filter. The gas scrubbing action serves to clean the filter and allows it to operate without clogging for weeks and months. Nutrient feed is pumped into the bioreactor and the harvest filtrate is removed continuously, or at periodic intervals.

The present invention provides an inexpensive perfusion filtration system that does not require any external loop or recirculation pump. Thus, it is much simpler, has lower cost, and is less prone to contamination than conventional devices.

The perfusion bioreactor may be used to produce secreted products, produce large amounts of slow growing cells, or function as an artificial organ such as an extracorporeal liver. The simple construction and sterile design of the filter assembly make it ideal for hospital use in cell and gene therapy applications.

DETAILS OF THE INVENTION

Figure 1A:
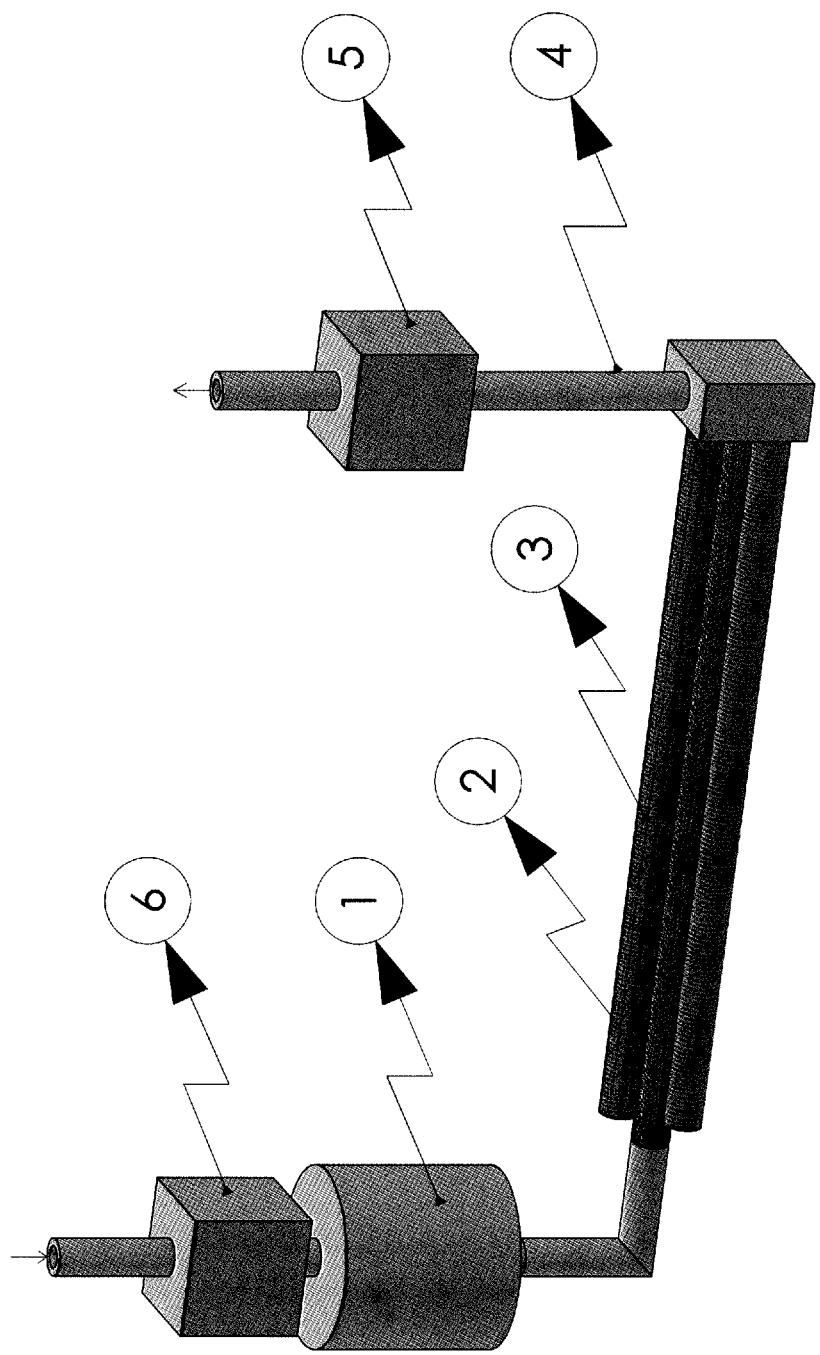
FIG. 1. Cross sectional (a) and bottom (b) view of the filter assembly.

The process of water purification was described in writings in ancient Greek and Sanskrit as early as 2000 BCE. Methods utilized by these peoples included sand and gravel filtration, straining and boiling. While the science of filtration may not have been evident to early inventors, today, the science of filtration has yielded some of the most significant invention in the art of separation if components, not just dissolved and undissolved but even types of dissolved components. The most common type of filtration would be to force the solution through a membrane of finite pore size that would retain the smallest size of the component to be separated. Often, it is filtrate that is desired but mostly it is the filtered material.

Microfiltration refers to removing very fine particles including bacteria and cells; a typical sterilizing filter would have a pore size of about 0.22 microns, however, in many biological processes, such small pore size is not necessary since the purpose is to remove a certain mass of cells, whose size is well known. For example, the Chinese Hamster Ovary cells, the most common engine for recombinant expression of proteins takes a filter of about 5 microns in diameter to filter out. It is important to realize that the smaller the pore size, the greater is the pressure required to force the flow of liquid and greater is the chance of blocking the pores. As a result, microfiltration has been replaced by other means such as centrifugation to remove cells in many industrial processes. However, if a system can be developed wherein large quantities of suspended cells can be removed without blocking the filters, this would always be preferred as it obviates the need for another unit process.

The instant invention offers a novel solution in the art of filtration wherein the filters are kept from getting blocked through continuous scrubbing by fine gas bubbles. Introduction of gas bubbles will have additional benefits in improving aeration and the process of aeration can be utilized for a dual purpose in some situations, to grow cells and to filter out cells in the same container and at the same time with remarkable cost and timesaving.

Figure 1B:
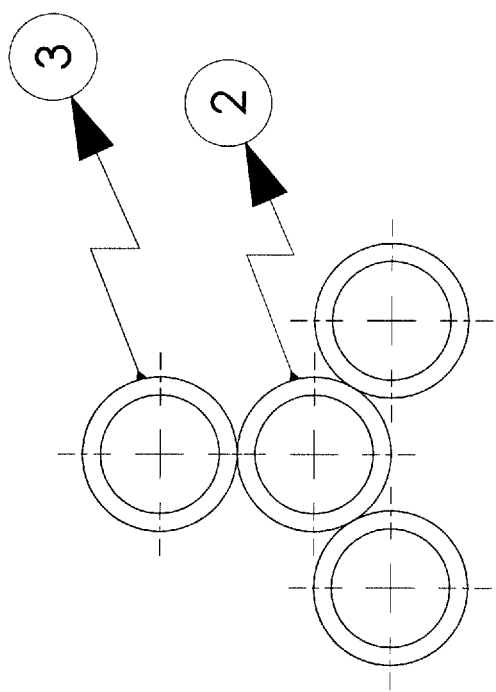

For the purposes of illustrating the invention, there is shown in the drawings a form which is presently preferred, it being understood however, that the invention is not limited to the precise form shown by the drawing in which:

FIG. 1 is a cross-sectional view (a) and a bottom view (b) of the filter assembly.

FIG. 1 describes a preferred embodiment of the invention. A gas filter (1) is attached to a tubular ceramic gas sparger (2) to sterilize the gas coming into the gas sparger that is surrounded by three tubular ceramic perfusion filters (3), which are connected to a source of vacuum (5) through a harvest tube (4). In addition, there is an adjustable valve (6) on the gas inlet tube. Alternately, both ends of the gas sparger may have an inlet and both ends of the perfusion filter may have harvest tubes attached to it. The gas sparger and the perfusion filter are bound together with nylon or metallic ties (not shown) such that the surface of the gas sparger is in direct contact with the surface of the perfusion filters. The entire filter assembly can be placed inside a tube to make the device portable.

The perfusion filter 3 is made of a material of suitable porosity to retain cells. Two designs for the perfusion filter are disclosed. One where a hollow tube made of a solid polymer material and having numerous perforations is wrapped around or sheathed with a sintered porous polyethylene sheet with a mean pore size of 7 microns (Porex T3). The porous polyethylene has the advantage of a very smooth surface and is electrically charged such that the cells are inhibited from attaching to the surface of the filter 3. The polypropylene material can also be easily heat welded. Other suitable plastics such as nylon and polyethylene could also be used. The filtration membrane is heat welded to the hollow perforated tube. A hose barb port can be attached to the hollow tube so that the harvest tube 4 may be easily attached. This design also obviates the problems associated with the disclosures in U.S. Pat. No. 6,544,788 where a polyethylene mesh is stuffed inside the filter to prevent the filtration membrane from being sucked flat against the upper layer of the filter and choking off flow. The prior art admits these shortcomings that makes it useful only for limited applications.

The pore size of the perfusion filter is important and dependent on the specific process for which it is used; generally, the average diameter of CHO cells is 14-15 microns but here is a distribution of sizes with a sharp fall in the distribution below 8 microns; so while, a 7 micron filter (as used in U.S. Pat. No. 6,544,788) will be useful, it leaves the possibility of losing a substantial number of cells smaller than 7 microns in size. The instant invention set a limit of 5 micros for the perfusion filter as the cut off for more 99% CHO cells while maintaining the fast flow through the filter. Other methods such as U.S. Pat. No. 65,544,788 can not afford to use a smaller size filter because of the blockage that can easily occur with smaller pore sizes as they produce a greater filtration pressure.

In the second design disclosed in the instant invention, the need for a filter membrane is obviated by using a hard tube as a perfusion filter with porosity of less than 5 microns to act as the filter. This tube can be made of various materials but preferably ceramic materials and more specifically aluminum oxide. Additionally, this hard walled structure that acts as a filter can be made in many shapes and forms including discs, cuboid, rectangular, etc., to fit any need of the application. Ceramic materials are inexpensive, offer high consistency in their porosity and extremely robust in handling physical pressure. Alternate materials of construction can be used including polymeric and metallic. The key to the second design is that the filter material itself provides the support to the filter structure and thus provides a very large surface area available for filtration. The tubular structure has two openings and both of these can be used to draw the liquid out or one can be blocked to meet specific requirements of use.

In both instances, a sparging filter is used to generate fine gas bubbles in the range of 10 to 1000 microns in diameter to strike them the perfusion filter surface to swiftly, yet forcibly remove any cells that might adhere to the filter surface under the negative pressure of nutrient media as it is being sucked into the pores of the filters. Several designs of the sparging filter are possible but the preferred embodiment is a ceramic sparging filter that allows for bubbles to be created along a wider surface area and in most instances, the sparging filter can be made of same dimension as the perfusion filter to allow treating the perfusion filter along its entire length.

An ideal combination is found when both filters have tubular shapes so that several perfusion filters that are scrubbed can be arranged around the sparging filter providing maximum efficiency of sparging filter.

Almost infinite assemblies can be made where the perfusion filter and the sparging source are arranged but to make it most effective, the distance between the perfusion filter and the sparging source can be critical. It is well known that bubbles coalesce to larger size bubbles under the thermodynamic reduction of free surface energy. Smaller bubbles are desirable for several reasons, first they provide a broader cover to the surface and secondly, the smaller size does not cause compression of the cells against the filter wall. Keeping the sparging filter closest to the surface of the perfusion filter would make the process of cleansing the surface of the perfusion filter most efficient. It is for this reason, it was disclosed that a distance of 10 microns to 5 mm between the perfusion filter and the sparging source is the most optimal.

To make sure that the bubbles formed are of fine size, the sparging filters would have very fine porosity, generally around 1 microns; as a rule, a 1 micron pore would yield a 10 micron bubble (depending on many physicochemical factors of the media) and would rapidly grow to a size of 100 microns within a few mm of its discharge. As a result, the instant invention reports a preferred embodiment as a sparging filter made of ceramic material with a porosity of 1 micron.

The filter assembly comprising a perfusion filter and a sparging filter attached together are placed inside the bioreactor and the harvest tube 4 is connected to a source of vacuum using flexible tubing so that the filtrate can be removed from the bioreactor. It is preferable that this tubing be flexible enough to permit the use of a peristaltic pump to remove the liquid, yet rigid enough not to collapse under the vacuum pressure. The perfusion filter assembly and the sparging filter are sterilized in situ by gamma radiation.

Supplying sterile gas through the sparging filter precedes starting the withdrawn of cell-free filtrate through the perfusion filter and collection in an outside vessel. Equal amount of feed is added to provide nutrients and to keep the quantity of nutrient media constant inside the bioreactor. The perfusion operation puts the cells into a steady-state operation and can be extended for many weeks and even months. Perfusion operations require that nutrients be fed at a slow rate to the bioreactor. At the same time, liquid must be removed from the bioreactor to keep the volume reasonably constant and to remove toxic metabolic byproducts. In the case of secreted products, this harvest liquid may contain the product to be purified. In perfusion operation it is critical that cells not be allowed to leave the bioreactor. Otherwise, the cell concentration in the bioreactor will drop due to washout of the cells. In practice, a small amount of cell loss (<10%) is tolerated in order to remove dead and dying cells and to promote a low level of cell regrowth.

In a first embodiment, the instant invention discloses a filtration assembly comprising a perfusion filter capable of separating suspended cells from the media, a gas sparger and an arrangement of the two in such configuration that the outer surface of the perfusion filter is continuously bathed in the fine bubble created by the sparging filter. This allows continuous scrubbing of the external surface of the perfusion filter and keeping the surface clean at all time for long-term perfusion.

In a second embodiment, the instant invention discloses a design of a perfusion filter comprising a hard tubular structure with perforated surface, which is sheathed with a filter membrane of any type; the tubular structure provides the support to the filter membranes, which are often delicate and flexible.

In a third embodiment, the instant invention discloses the use of ceramic material structures such as tube, disc, ovoid or rectangle to serve as perfusion filter with pore sizes of 5 micron or less.

In a third embodiment, the instant invention disclose the use of ceramic material structures such as tube, disc, ovoid or rectangle to serve as sparging filter with pore size of 10 micron or less.

In a fourth embodiment, the instant invention discloses myriad of possibilities of assembling the perfusion filter and the sparging filter to achieve the scrubbing of the perfusion filter.

In a fifth embodiment, the instant invention discloses a dual use of the sparging to scrub the outer surface of perfusion filter as enhancing the growth of cell culture in a bioreactor.

In a sixth embodiment, the instant invention discloses a method of perfusion to recover biological products from a bioreactor and to allow long-term operation of bioreactors by retaining the cell culture within the bioreactor; the dual use also extends to preservation or organs by perfusion wherein aeration would provide additional source of nutrition to the tissue being preserved. The choice of gas to scrub is based on a cost factor but the choice can also have a dual use wherein the selected gas can enhance the activity of culture media. Generally, where no additional benefit is sought from the choice of gas, the obvious choice should be air because its lowest cost but it could also be any inert gas where the use of air may not be advised. In most instances the choice would be nitrogen gas.

In a seventh embodiment, the instant invention provides a inexpensive solution for perfusion filtration in every type of biological process.

In an eight embodiment, the instant invention provides means of adjusting the intensity of gas bubbles by monitoring the amount of vacuum needed to draw a pre-determined volume of liquid and thus assuring that the perfusion filter is kept clean, The components of the filtration devices described herein which come into contact with the culture medium or products provided thereby desirably comprise biocompatible materials, more desirably biocompatible polymers, and are preferably sterilizable.

It should also be understood that many of the components described herein also are desirably flexible, e.g., the containers desirably comprise flexible biocompatible polymer containers (such as collapsible bags), with the conduits also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A gas-scrubbed filtration device to remove a liquid from a suspension comprising:
   (a) at least one perfusion filter, wherein the perfusion filter is a tube or cylinder, and wherein at least one surface and connected to a source of vacuum through a harvest tube and disposed in the suspension;
   (b) at least one sparging filter, wherein the sparging filter is a tube or a cylinder, connected to a source of compressed gas and capable of blowing gas bubbles of 10-1000 micron diameter in size and disposed in the suspension;
   (c) fixing the perfusion filter and the sparging filter in such configuration as to allow optimal contact of gas bubbles from sparging filter with the surface of the perfusion filter, wherein the perfusion filters and the sparging filter are set apart at least 10 μm to no more than 50 mm along the entire surface of the perfusion filter and sparging filter;
   (d) a vacuum source to maintain a level of vacuum needed to draw a pre-determined volume of the liquid out of the suspension;
   (e) and wherein the source of compressed gas comprises an adjustable flow rate valve to adjust the flow rate of gas thereby increasing or decreasing scrubbing at the surface of the perfusion filter.

2. The filtration device according to claim 1, wherein the perfusion filter is made of polymer, metal or ceramic material.

3. The filtration device according to claim 1, wherein the gas is air, nitrogen, oxygen, carbon dioxide or argon.

4. The filtration device according to claim 1, wherein the gas flow rate is automatically adjusted by control mechanism that monitors the amount of vacuum needed to maintain a certain withdrawal of liquid.

5. The filtration device according to claim 1, wherein the perfusion filter comprises a hollow perforated tube sheathed with a synthetic membrane filter.

6. The filtration device according to claim 5, wherein the sheath is made of sintered polyethylene or nylon.

7. The filtration device according to claim 1, wherein the sparging filter is made of polymer, metal or ceramic material.

8. The filtration device according to claim 1, wherein a plurality of perfusion filters are assembled around a sparging filter.

9. The filtration device according to claim 1, wherein a plurality of sparging filters are assembled around a perfusion filter.

10. The filtration device according to claim 1, wherein the pore size of the perfusion filters is less than 5 μm.

11. The filtration device according to claim 1, wherein the pore size of the sparging filters is less than 10 μm.

12. The filtration device according to claim 1, wherein the pore size of the sparging filters is less than 1 μm.

13. The filtration device according to claim 1, wherein the vacuum source is a peristaltic pump operating on the harvest tube attached to the perfusion filter.

14. The filtration device according to claim 1, wherein the suspension comprises a nutrient media and a biological culture.

15. The filtration device according to claim 1, wherein said filter device is sterilized in situ in a disposable bioreactor.

16. The filtration device according to claim 1, wherein the compressed gas is first passed through a sterilizing filter before passing it through the sparging filter.

* * * * *